(12) United States Patent
Hajduk et al.

(10) Patent No.: US 7,112,443 B2
(45) Date of Patent: Sep. 26, 2006

(54) HIGH THROUGHPUT PERMEABILITY TESTING OF MATERIALS LIBRARIES

(75) Inventors: Damian A. Hajduk, San Jose, CA (US); Oleg Kolosov, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 554 days.

(21) Appl. No.: 10/274,184

(22) Filed: Oct. 18, 2002

(65) Prior Publication Data

US 2004/0077091 A1    Apr. 22, 2004

(51) Int. Cl.
*G01N 31/00* (2006.01)
*G01N 15/08* (2006.01)
*G01N 33/44* (2006.01)

(52) U.S. Cl. .................. 436/5; 73/38; 422/99; 422/104; 436/3; 436/39; 436/127; 436/136; 436/138; 436/181

(58) Field of Classification Search .............. 436/3, 436/5, 39, 127, 136, 138, 183, 181; 73/38; 422/99, 104
See application file for complete search history.

(56) References Cited

U.S. PATENT DOCUMENTS

| | | |
|---|---|---|
| 1,870,412 A | 8/1932 | Kennedy |
| 3,071,961 A | 1/1963 | Heigl et al. |
| 3,301,043 A * | 1/1967 | Lyssy ............................ 73/38 |
| 3,675,475 A | 7/1972 | Weinstein |
| 3,713,328 A | 1/1973 | Aritomi |
| 3,798,960 A | 3/1974 | Glass |
| 3,805,598 A | 4/1974 | Corcoran |
| 3,818,751 A | 6/1974 | Karper et al. |
| 3,849,874 A | 11/1974 | Jeffers |
| 3,895,513 A | 7/1975 | Richardson |
| 3,908,441 A | 9/1975 | Virloget |
| 3,933,032 A | 1/1976 | Tschoegl |
| 4,229,979 A | 10/1980 | Greenwood |
| 4,447,125 A | 5/1984 | Lazay et al. |
| 4,517,830 A | 5/1985 | Gunn et al. |
| 4,567,774 A | 2/1986 | Manahan et al. |
| 4,570,478 A | 2/1986 | Soong |
| 4,599,219 A | 7/1986 | Cooper et al. |
| 4,602,501 A | 7/1986 | Hirata |
| 4,605,589 A | 8/1986 | Orphanides |
| 4,680,958 A | 7/1987 | Ruelle et al. |
| 4,685,328 A | 8/1987 | Huebner et al. |
| 4,699,000 A | 10/1987 | Lashmore et al. |
| 4,715,007 A | 12/1987 | Fujita et al. |
| 4,740,078 A | 4/1988 | Daendliker et al. |

(Continued)

FOREIGN PATENT DOCUMENTS

EP    0 317 356    5/1989

(Continued)

OTHER PUBLICATIONS

Landrock, A. H. et al, Tappi 1952, 35, 241-246.*

(Continued)

*Primary Examiner*—Arlen Soderquist
(74) *Attorney, Agent, or Firm*—Dobrusin & Thennisch PC

(57) ABSTRACT

A library of material samples is screened for properties such as permeability. A library of material samples is provided. A stimulus such as an exposure to a permeate fluid is provided to each member of the library. A response of each of the material samples due to the stimulus is measured and the response, the stimulus or both are recorded and related to provide data. Thereafter, the data is analyzed to reach conclusions regarding the properties of the material samples.

26 Claims, 7 Drawing Sheets

U.S. PATENT DOCUMENTS

| | | |
|---|---|---|
| 4,749,854 A | 6/1988 | Martens |
| 4,789,236 A | 12/1988 | Hodor et al. |
| 4,793,174 A | 12/1988 | Yau |
| 4,829,837 A | 5/1989 | Telfer |
| 4,893,500 A | 1/1990 | Fink-Jensen |
| 4,899,575 A | 2/1990 | Chu et al. |
| 4,899,581 A | 2/1990 | Allen et al. |
| 4,932,270 A | 6/1990 | Lurie et al. |
| 4,975,320 A | 12/1990 | Goldstein et al. |
| 5,008,081 A | 4/1991 | Blau et al. |
| 5,015,856 A * | 5/1991 | Gold ............... 250/339.09 |
| 5,051,239 A | 9/1991 | von der Goltz |
| 5,092,179 A | 3/1992 | Ferguson |
| 5,115,669 A | 5/1992 | Fuller et al. |
| 5,142,900 A | 9/1992 | Duke |
| 5,193,383 A | 3/1993 | Burnham et al. |
| 5,236,998 A | 8/1993 | Lundeen et al. |
| 5,269,190 A | 12/1993 | Kramer et al. |
| 5,271,266 A | 12/1993 | Eschbach |
| 5,272,912 A | 12/1993 | Katsuzaki |
| 5,280,717 A | 1/1994 | Hoseney et al. |
| 5,303,030 A | 4/1994 | Abraham et al. |
| 5,305,633 A | 4/1994 | Weissenbacher et al. |
| 5,398,885 A | 3/1995 | Andersson et al. |
| 5,437,192 A | 8/1995 | Kawamoto et al. |
| 5,438,863 A | 8/1995 | Johnson |
| 5,452,614 A | 9/1995 | Kato et al. |
| 5,452,619 A | 9/1995 | Kawanabe et al. |
| 5,481,153 A | 1/1996 | Turner |
| 5,517,860 A | 5/1996 | Lin et al. |
| 5,520,042 A | 5/1996 | Garritano et al. |
| 5,532,942 A | 7/1996 | Kitamura et al. |
| 5,610,325 A | 3/1997 | Rajagopal et al. |
| 5,626,779 A | 5/1997 | Okada |
| 5,699,159 A | 12/1997 | Mason |
| 5,700,953 A | 12/1997 | Hlady et al. |
| 5,723,792 A | 3/1998 | Miyazaki |
| 5,728,532 A | 3/1998 | Ackley |
| 5,756,883 A | 5/1998 | Forbes |
| 5,764,068 A | 6/1998 | Katz et al. |
| 5,776,359 A | 7/1998 | Schultz et al. |
| 5,817,947 A | 10/1998 | Bergerus |
| 5,821,407 A | 10/1998 | Sekiguchi et al. |
| 5,847,283 A | 12/1998 | Finot et al. |
| 5,877,428 A | 3/1999 | Scolton |
| 5,892,157 A | 4/1999 | Syre |
| 5,922,967 A | 7/1999 | Motoyama |
| 5,959,297 A | 9/1999 | Weinberg et al. |
| 5,985,356 A | 11/1999 | Schultz et al. |
| 5,999,887 A | 12/1999 | Giannakopoulos et al. |
| 6,004,617 A | 12/1999 | Schultz et al. |
| 6,010,616 A | 1/2000 | Lewis et al. |
| 6,013,199 A | 1/2000 | McFarland et al. |
| 6,024,925 A | 2/2000 | Little et al. |
| 6,030,917 A | 2/2000 | Weinberg et al. |
| 6,033,913 A | 3/2000 | Morozov et al. |
| 6,034,240 A | 3/2000 | La Pointe |
| 6,034,775 A | 3/2000 | McFarland et al. |
| 6,040,193 A | 3/2000 | Winkler et al. |
| 6,043,317 A | 3/2000 | Mumick et al. |
| 6,043,363 A | 3/2000 | LaPointe et al. |
| 6,045,671 A | 4/2000 | Wu et al. |
| 6,050,138 A | 4/2000 | Lynch et al. |
| 6,050,139 A | 4/2000 | Bousfield et al. |
| 6,087,181 A | 7/2000 | Cong |
| 6,092,414 A | 7/2000 | Newman |
| 6,124,476 A | 9/2000 | Guram et al. |
| 6,149,882 A | 11/2000 | Guan et al. |
| 6,151,123 A | 11/2000 | Nielsen |
| 6,157,449 A | 12/2000 | Hajduk |
| 6,175,409 B1 | 1/2001 | Nielsen et al. |
| 6,177,528 B1 | 1/2001 | LaPointe et al. |
| 6,182,499 B1 | 2/2001 | McFarland et al. |
| 6,187,164 B1 | 2/2001 | Warren et al. |
| 6,203,726 B1 | 3/2001 | Danielson et al. |
| 6,225,487 B1 | 5/2001 | Guram |
| 6,225,550 B1 | 5/2001 | Hornbostel et al. |
| 6,230,548 B1 | 5/2001 | Han et al. |
| 6,242,623 B1 | 6/2001 | Boussie et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,265,601 B1 | 7/2001 | Guram et al. |
| 6,268,513 B1 | 7/2001 | Guram et al. |
| 6,294,388 B1 | 9/2001 | Petro |
| 6,296,771 B1 | 10/2001 | Miroslav |
| 6,306,658 B1 | 10/2001 | Turner et al. |
| 6,315,923 B1 | 11/2001 | Devenney et al. |
| 6,326,090 B1 | 12/2001 | Schultz et al. |
| 6,336,353 B1 | 1/2002 | Matsiev et al. |
| 6,371,640 B1 | 4/2002 | Hajduk et al. |
| 6,383,815 B1 * | 5/2002 | Potyrailo ............... 436/2 |
| 6,393,895 B1 | 5/2002 | Matsiev et al. |
| 6,393,898 B1 | 5/2002 | Hajduk et al. |
| 6,406,632 B1 | 6/2002 | Safir et al. |
| 6,541,271 B1 | 4/2003 | McFarland et al. |
| 2002/0162384 A1 * | 11/2002 | Sharp et al. ............... 73/38 |
| 2003/0219716 A1 * | 11/2003 | Avdeef et al. ............... 435/4 |
| 2004/0023303 A1 * | 2/2004 | Reppy et al. ............... 435/7.1 |
| 2004/0077075 A1 * | 4/2004 | Jensen et al. ............... 435/297.2 |

FOREIGN PATENT DOCUMENTS

| | | |
|---|---|---|
| EP | 1 158 290 A2 | 11/2001 |
| JP | 402297040 A | 12/1990 |
| WO | WO 96/11878 | 4/1996 |
| WO | WO 98/15501 | 4/1998 |
| WO | WO 99/15888 | 4/1999 |
| WO | WO 99/18431 | 4/1999 |
| WO | WO 00/17413 | 3/2000 |
| WO | WO 00/22436 | 4/2000 |
| WO | WO 00/23921 | 4/2000 |
| WO | WO 00/36410 A1 | 6/2000 |
| WO | WO 00/40331 | 7/2000 |
| WO | WO 00/51720 | 9/2000 |
| WO | WO 00/67086 | 11/2000 |
| WO | WO 01/79949 A2 | 10/2001 |

OTHER PUBLICATIONS

Pye, D. G. et al, Journal of Applied Polymer Science 1976, 20, 287-301.*
Bigu, J. Nuclear Instruments & Methods in Physics Research 1986, A251, 366-373.*
Alger, M. M. et al, Journal of Membrane Science 1989, 40, 87-99.*
Chalykh, T. I. et al, Chemical Abstracts 1989 abstract 111:135541.*
Orchard, G. A. J. et al, Journal of Polymer Science, Part B: Polymer Physics 1990, 28, 603-621.*
Kimmerle, K. et al, Journal of Membrane Science 1991, 61, 1-17.*
Larsson, A. C. et al, Journal of Membrane Science 1993, 84), 139-150.*
Steriotis, T. A. et al, Review of Scientific Instruments 1996, 67, 2545-2548.*
Kwak, S.-Y. et al, Journal of Polymer Science, Part B: Polymer Physics 1996, 34, 2201-2208.*
Tourreuil, V. et al, New Journal of Chemistry 1998, 22, 1463-1468.*
Jons, S. et al, Journal of Membrane Science 1999, 155, 79-99.*
Pieracci, J. et al, Journal of Membrane Science 1999, 156, 223-240.*
Yeom, C. K. et al, Journal of Membrane Science 2000, 166, 71-83.*
Kim, T.-J. et al, Sensors and Actuators B 2001, 72, 11-20.*
Togawa, J. et al, Journal of Membrane Science 2001, 188, 39-48.*
Dai, Y. et al, Journal of Membrane Science 2001, 188, 195-203.*
Scarpello, J. T. et al, Journal of Membrane Science 2002, 203, 71-85.*

Lundstrom, T. et al, Polymer Composites 1999, 20, 146-154.*
Ayub, M. et al, Petroleum Science and Technology 2001, 19, 1129-1154.*
Rosen, B. et al, Journal of Polymer Science 1957, 25, 225-228.*
Forte, R. et al, Journal of Applied Polymer Science 1992, 45, 1473-1483.*
Tabe Mohammadi, A. et al, Journal of Membrane Science 1995, 98, 281-286.*
Campbell Ritchie, A. et al, Journal of Membrane Science 1996, 121, 169-174.*
Young, W.C., Roark's Formulas for Stress and Stain, 1989, pp. 398+429.
Timoshenko, S., Theory of Plates and Shells, McGraw-Hill, New York 1940, pp. 50-57, 62-79.
Osterberg, Peter M. and Stephen D. Senturia, "M-TEST: A Test Chip for MEMS Material Property Measurement Using Electrostatically Actuated Test Structures," Journal of Microelectromechanical Systmes, vol. 6, No. 2, Jun. 1997, 107-118.
Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223-228.
Grover, G. et al., "A Screening Technique for Fabric Handle", J. Text. Inst., 1993, 84 No. J. Textile Institute, pp. 486-494.
Pan, Ning and K.C. Yen, "Physical Interpretations of Curves Obtained Through the Fabric Extraction Process for Handle Measurement," Textile Research Journal 62(5), pp. 279-290 (1992).
"Handle-O-Meter", Thwing-Albert Instrument Company, Philadelphia, PA.

Raeel, Mastura and Jiang Liu, "An Empirical Model for Fabric Hand" Textile Research Journal 62, 1, pp. 31-38 (1991).
Ali, S.I. and Shahida Begum, "Fabric Softeners and Softness Perception", Ergonomics, v. 37, No. 5, pp. 801-806 (1994).
"DMA 2980 Dynamic Mechanical Analyer," http://www.tainst.com/dma2.html, Dec. 29, 2000.
"Introducing the NEW DMTA V!", http://www.rheometricscientific.com/dmtaV.htm, Dec. 29, 2000.
"Stand Test Method for Rubber Property-Intrenational Hardness," American Society for Testing and Materials.
Amitay-Sadovsky, Ella and H. Daniel Wagner, "Evaluation of Young's Modulus of Polymers from Knoop Microindentation Tests" Polymer Communications, 1998, vol. 39, No. 11, pp. 2387-2390.
Calleja, F.J. Balta, "Microhardness Studies of Polymers and Their Transistions" TRIP, Dec. 1994, vol. 2, No. 12, pp. 419-425.
Bowlt, C., "A Simple Capillary Viscometer" Physics Education, Mar. 1975, vol. 10, No. 2, pp. 102-103.
Lacombe, Robert H. and Jeremy Greenblatt, "Mechanical Propoerties of Thin Polyimide Films" pp. 647-668.
Shinozaki, D.M. and Y. Lu, "Micro-Indentation Relaxation Measurements in Polymer Thin Films" Journal and Electric Materials, 1997, vol. 26, No. 7, pp. 852-858.
Wierenga, P.E. and A.J.J. Franken, "Ultramicroindentation Apparatus for the Mechanical Characterization of Thin Films" J. Appl. Phys., Jun. 15, 1984, 55 (12).

* cited by examiner

HIGH THROUGHPUT PERMEABILITY TESTING OF MATERIALS LIBRARIES

TECHNICAL FIELD

The present invention generally relates to the field of materials characterization. In particular, the invention relates to high throughput screens for evaluating properties such as permeability of polymers or other materials.

BACKGROUND OF THE INVENTION

Currently, there is substantial research activity directed toward the discovery and optimization of polymeric and other materials for a wide range of applications. Although the chemistry of many materials reactions has been extensively studied, nonetheless, it is rarely possible to predict a priori the physical or chemical properties a particular material will possess or the precise composition and architecture that will result from any particular synthesis scheme. Thus, techniques to determine such properties are an essential part of the discovery process.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

The characterization of polymers or other materials using combinatorial methods has only recently become known. Examples of such technology are disclosed, for example, in commonly owned U.S. Pat. No. 6,182,499 (McFarland et al); U.S. Pat. No. 6,175,409 B1 (Nielsen et al); U.S. Pat. No. 6,157,449 (Hajduk et al); U.S. Pat. No. 6,151,123 (Nielsen); U.S. Pat. No. 6,034,775 (McFarland et al); U.S. Pat. No. 5,959,297 (Weinberg et al), all of which are hereby expressly incorporated by reference herein.

Of particular interest to the present invention are combinatorial methods and apparatuses for synthesizing or otherwise providing polymers and other materials followed by screening of those materials for characteristics such as permeability. Synthesis and screening of the materials for properties presents a multitude of challenges. As an example, conventional instruments and other apparatuses lack the ability to screen properties of several materials in rapid succession, in parallel, on a single substrate or a combination thereof. Thus, challenges are presented for building systems that can quickly process and test (either in parallel or in serial succession) mechanical properties of many materials. Additionally, challenges are presented for forming, processing or otherwise treating materials so that the materials are in appropriate condition for high throughput screening of properties.

Additional challenges are presented for rapidly measuring permeability of samples. Particularly, for relatively small samples it is difficult to design equipment that can properly support the relatively small samples. It can also be difficult to create instruments that will expose relatively small samples to permeation fluids (i.e., fluids that will permeate through a sample) in a consistent manner. Moreover, samples such as polymer films and other films, may experience internal conditions such as saturation, which can present challenges for creating instruments and methods that can provide comparable results for samples of different compositions or thicknesses.

SUMMARY OF THE INVENTION

In accordance with one preferred embodiment of the present invention, a method for screening an array of materials for a material property is provided. According to the method a library of at least four sample materials is provided. Each of the at least four sample materials is subjected to one or more fluids. A response of each of the at least four sample materials to the one or more fluids is monitored. Moreover, the response of the each of the at least four materials is correlated to the permeability of each of the at least four sample materials.

In accordance with another preferred embodiment of the present invention, a method for measuring permeability of polymer films is contemplated. According to the method, a single polymer film sample, or a library comprising at least four different material samples is provided. Thereafter, permeability of each of the sample materials is measured.

In yet another embodiment, the present invention contemplates a method for screening permeability of a plastic film material wherein a sample of the material is smaller than about 2 $cm^2$.

DETAILED DESCRIPTION OF THE PREFERRED EMBODIMENT

Figure 1:
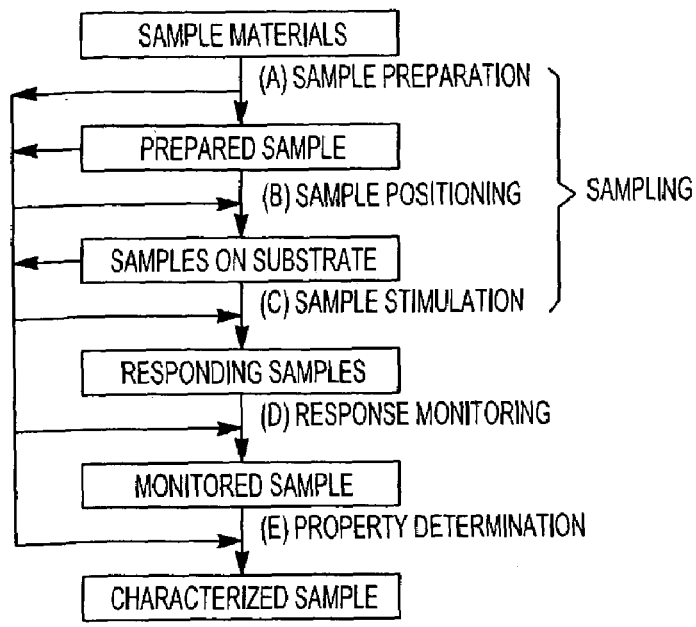
FIG. 1 is a flowchart of possible steps for methods of the present invention.

The term "permeability" herein refers to the tendency of a first material to allow a second material to pass through an article comprising the first material. Both the first and second materials may be solids, liquids, gasses, fluids or the like. It is also contemplated that the first and second materials may be the same as each other or different from each other.

The several aspects of the methods and systems disclosed and claimed herein can be advantageously employed separately, or in combination to efficiently analyze a variety of materials, with particular emphasis on solid materials, polymeric materials, liquid materials or flowable materials. The present invention may be employed as part of a high throughput research program. It may be also employed for on-line quality control, or for other analytical applications.

Combinatorial Approaches for Science Research

In a combinatorial approach for identifying or optimizing materials or reactions, a large compositional space (e.g., in the context of polymers; of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing libraries and then rapidly screening such libraries. By way of illustration, polymer libraries can comprise, for example, polymerization product mixtures resulting from polymerization reactions that are varied with respect to such factors.

Combinatorial approaches for screening a library can include an initial, primary screening, in which materials are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Because local performance maxima may exist in compositional spaces between those evaluated in the primary screening of the first libraries or alternatively, in process-condition spaces different from those considered in the first screening, it may be advantageous to screen more focused libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused libraries can continue as long as the high-throughput primary screen can meaningfully distinguish between neighboring library compositions or compounds.

Once one or more hits have been satisfactorily identified based on the primary screening, libraries focused around the primary-screen hits can be evaluated with a secondary screen—a screen designed to provide (and typically verified, based on known materials, to provide) chemical composition or process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular polymer materials, catalysts, reactants, polymerization conditions or post-synthesis processing conditions having characteristics that surpass the predetermined metrics for the secondary screen may then be considered to be "leads." If desired, additional polymer or polymerization product libraries focused about such lead materials can be screened with additional secondary screens or with tertiary screens. Identified materials may be subsequently developed for commercial applications through traditional bench-scale and/or pilot scale experiments.

While the concept of primary screens and secondary screens as outlined above provides a valuable combinatorial research model, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary, secondary or other screen, depending on the specific research program and goals thereof. See, generally, U.S. patent application Ser. No. 09/227,558 entitled "Apparatus and Method of Research for Creating and Testing Novel Catalysts, Reactions and Polymers", filed Jan. 8, 1999 by Turner et al., incorporated by reference for further discussion of a combinatorial approach to polymer science research. Bulk quantities of a particular material may be made after a primary screen, a secondary screen, or both.

According to the present invention, methods, systems and devices are disclosed that improve the steps necessary to characterize mechanical or physical properties of a material sample or a plurality of samples. In preferred embodiments, in the context of polymer analysis, a property of a plurality of polymer samples or of components thereof can be detected in a polymer characterization system with an average sample-throughput sufficient for an effective combinatorial polymer science research program.

Referring to FIG. 1, the systems and methods, preferably, start with a library or array of sample materials that may exhibit one or more predetermined physical/mechanical properties such as strength, tack, surface tension interfacial tension or the like. Ultimately, these predetermined properties will be determined in a determination step (Step E), however, several prior steps may be effected prior to Step E. The sample materials may be prepared such as by heating, cooling, or addition of additives. Such preparation is typically designed to affect the properties that are ultimately being determined. The sample materials may also be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample preparation (Step A) and sample positioning (Step B) may be optional steps in property determination protocols. Also sample preparation and sample positioning may be performed in any order if they are performed. Additionally it should be recognized that sequences other than the order of steps listed above are possible, and the above listing is not intended as limiting.

Typically, however, stimulation of the sample materials (Step C) is needed to effect one or more responses of the materials wherein the responses are related to the one or more physical properties that are being tested. Exemplary stimuli include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may be employed.

The responses of the materials are typically monitored (Step D) with hardware such as sensors, transducers, load cells or other like devices. Properties may be determined (Step E) quantitatively or qualitatively by relating the responses to the material properties.

A plurality of polymer samples may be characterized as described above in connection with FIG. 1. As a general approach for improving the sample throughput for a plurality of polymers, each of the steps (A) through (E) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

In preferred embodiments, permeability of a plurality of polymer samples or of components thereof can be analyzed with an average sample-throughput sufficient for an effective combinatorial polymer science research program.

The samples analyzed herein may be analyzed in a serial approach (e.g. rapid serial), a parallel approach, or a combination thereof. For example, a plurality of samples can be characterized with a single instrument in a rapid-serial approach in which each of the plurality of samples ($s_1, s_2, s_3 \ldots s_n$) are processed serially through the instrument with each of the steps effected in series on each of the of samples to produce a serial stream of corresponding property information ($p_1, p_2, p_3 \ldots p_n$).

As another example, a plurality of samples can be analyzed with two or more instruments in a pure parallel (or for larger libraries, serial-parallel) approach in which the plurality of samples ($s_1, s_2, s_3 \ldots s_n$) or a subset thereof are processed through the two or more measurement systems (I, II, III . . . N) in parallel, with each individual system effecting each step on one of the samples to produce the property information ($p_1, p_2, p_3 \ldots p_n$) in parallel.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified by parallel sample preparation of a plurality of samples ($s_1, s_2, s_3 \ldots s_n$), followed by measuring with a single apparatus to produce a serial stream of corresponding property information ($p_1, p_2, p_3 \ldots p_n$). In another exemplary parallel-series hybrid approach, a plurality of samples ($s_1, s_2, s_3 \ldots s_n$) are prepared, measured and correlated in a slightly offset (staggered) parallel manner to produce the property information ($p_1, p_2, p_3 \ldots p_n$) in the same staggered-parallel manner.

Optimization of individual characterization steps with respect to speed and quality of information can improve sample throughput regardless of whether the overall scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel protocols that may be employed.

Sample Materials

The samples for which the present invention is useful for screening include polymeric materials or any other liquid, flowable or solid material that is capable of being provided as a liquid, solid, gel or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers. Accordingly, unless otherwise stated, reference to polymers includes plastics incorporating such polymers.

In one embodiment, the polymer molecule of the polymer component is preferably, but need not be, a non-biological polymer. The polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule.

The particular composition of the polymer molecule is not critical. The material may be thermoplastic, thermoset or a mixture thereof. It may be a polycondensate, polyadduct, a modified natural polymer. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), polypropylene, poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, polyacetals, cellophanes. Polymers also preferably include elastomer containing materials. Exemplary elastomers include neoprene, latex, butene, fluoroelastomers, fluorosilicones, silicone rubbers, epdm, foam rubber, polybutadiene, combinations thereof or the like.

Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or and an additional phase which may be a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a fluid state, with the resulting material constituting a liquid sample. Heating may be performed simultaneously while the samples are on a common substrate. Alternatively, the samples might be heated to a liquid state and then transferred (e.g., manually or with an automated sampler) to a common substrate, where it is heated to maintain its liquid state. In yet another embodiment, the sample is heated to liquefy it or maintain its liquidity while being transferred to a common substrate (e.g., while in a probe of an automated sampler).

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g. temperature moisture, radiation, chemicals, etc.), aged, or the like. It is also contemplated that an environmental controller may be employed for controlling environment exposure during testing of the samples.

In other preferred embodiments, polymer or other sample materials may be provided as solids or semi-solids. Such samples may be provided in a variety of geometric configurations such as blocks, cylinders, loops, films and the like. Generally, geometric configurations are selected to be appropriate for one or more tests that are to be performed upon the samples. Solid and semi-solid samples may be rigid, elastic, gelatinous or otherwise. In one preferred embodiment, samples are provided in a tacky state, and thus exhibits at least some degree of adhesiveness within the range of temperature under examination. Samples may also be specifically arranged for testing. For example, samples may be interwoven as a fabric, unwoven, machined to shape, molded to shape, cut to shape or otherwise physically manipulated for testing.

Other sample types and configurations, both polymer and non-polymer, are disclosed in commonly owned patent applications Ser. No. 09/939,252, filed Aug. 24, 2001, titled "High Throughput Mechanical Rapid Serial Property Testing of Materials Libraries"; Ser. No. 09/939,139, filed Aug. 24, 2001, titled, "High Throughput Fabric Handle Screening; Ser. No. 09/939,263, filed Aug. 24, 2001, titled "High Throughput Mechanical Property Testing of Materials Libraries Using Capacitance"; all three of which are expressly incorporated herein by reference for all purposes.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more typically from about 5 micrograms to about 1000 micrograms, and still more typically from about 20 micrograms to about 50 micrograms, alternatively individual samples occupy no more than about 100 mm$^2$ of area, and more preferably no more than about 50 mm$^2$, particularly when the samples are supported on a substrate.

Libraries of Sample Materials

Libraries of samples have 2 or more samples that are physically or temporally separated from each other—for example, by residing in different regions of a common substrate, in different sample containers of a common substrate, by having a membrane or other partitioning material positioned between samples, or otherwise. The plurality of samples preferably has at least 4 samples and more preferably at least 8 samples for screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include sub-groups of members of different libraries, or it may include combinations of plural libraries.

Typically, however, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

In instances when a substrate is employed for supporting a sample, the substrate can be a structure having a rigid or semi-rigid surface on which or into which the library of samples can be formed, mounted, deposited or otherwise positioned. The substrate can be of any suitable material, and preferably includes materials that are inert with respect to the polymer samples of interest, or otherwise will not materially affect the mechanical or physical characteristics of one sample in an array relative to another. Organic and inorganic polymers may also be suitably employed in some applications of the invention. Exemplary polymeric materials that can be suitable as a substrate material in particular applications include polyimides such as Kapton™., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

A library of polymer samples may be prepared in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT Pat. Application WO 96/11878.

Non-Polymer Sample Materials

Although several of the primary applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. For purposes herein, oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal compounds, metal oxides, metal salts, metal colloids, metal ligands, etc . . . , without particular limitation. Other materials, which may be characterized according to the present invention include, without limitation, ceramic materials, semiconducting and conducting materials, metals and composites. Still other materials for which the present application finds utility are discussed elsewhere herein.

Sampling/Auto-Sampler

In the general case, sample handling can be effected manually, in a semi-automatic manner or in an automatic manner.

Handling

Figure 4A:
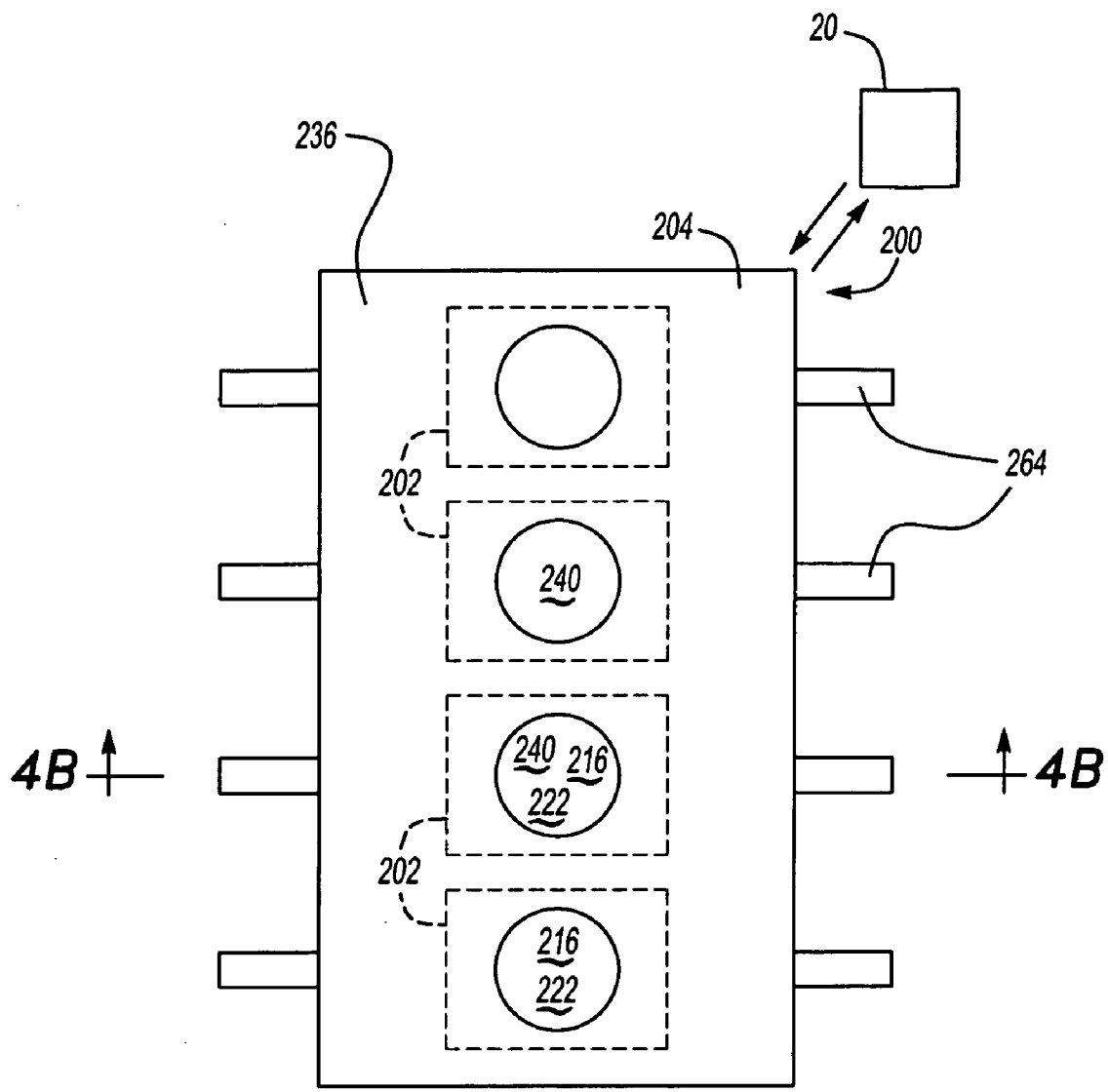
FIGS. 4A and 4B are respectively a top schematic view and a side schematic sectional view of another system for assisting in determining permeability of materials in accordance with the present invention.

In one embodiment, handling may be done using a microprocessor controlling an automated system (e.g., a robot arm 20) as shown in FIG. 4A. Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers).

Sample handling optionally may be effected with an auto-sampler having a heated injection probe (tip). An example of one such auto sampler is disclosed in U.S. Pat. No. 6,175,409 B1 (incorporated by reference).

Analytical Systems and Methods

According to the present invention, one or more systems, methods or both are used to determine the permeability of one or a plurality of material samples, and more preferably polymer films. Though manual or semi-automated systems and methods are possible, preferably an automated system or method is employed. A variety of automatic systems are available for automatically or programmably providing predetermined motions for handling, contacting, dispensing, or otherwise manipulating materials in solid, fluid liquid or gas form according to a predetermined protocol and thus enabling rapid throughput analysis of sample materials.

Figure 2:
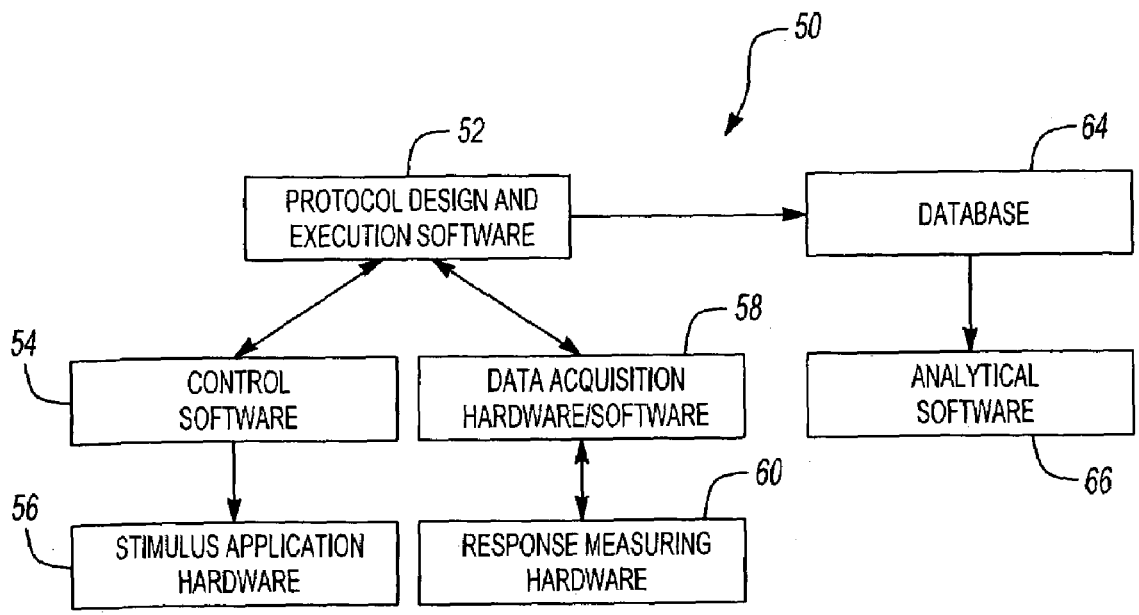
FIG. 2 is a block diagram of a potential platform system for executing methods and for operating systems.

Referring to FIG. 2, there is a flow schematic diagram of an exemplary automated system 50 for rapid determination of mechanical properties of several samples of material. Generally, the system 50 includes a suitable protocol design and execution software 52 that can be programmed with information such as synthesis, composition, location information or other information related to a library of materials positioned with respect to a substrate. The protocol design and execution software is typically in communication with control software 54 for controlling stimulus application hardware 56 or other automated systems. The protocol design and execution software 52 is also in communication with data acquisition hardware/software 58 for collecting data from response measuring hardware 60. Preferably, the control software 54 commands the stimulus application hardware 56 to apply stimuli to sample materials to evoke a response from the materials. At substantially the same time, the response measuring hardware 60 (e.g., sensors, transducers, load cells and the like) monitors the responses of the materials, the stimuli being applied to the materials or both, and provides data on the responses to the data acquisition hardware/software 58. Thereafter, the control software 54, the data acquisition hardware/software 58 or both transmit data to the protocol design and execution software 52 such that the sample materials or information about the sample materials may be matched with their responses to the applied stimuli and transmitted at data to a database 64. Once the data is collected in the database, analytical software 66 may be used to analyze the data, and more specifically, to determine mechanical properties of the sample materials, or the data may be analyzed manually.

Though not critical to the operation of the present invention, in one preferred embodiment, the system may be driven by suitable software, such as LIBRARY STUDIO™, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.) or a combination thereof. Moreover, data collected or produced by the system may be viewed using other suitable software such as POLYVIEW™, by Symyx Technologies, Inc. (Santa Clara, Calif.). The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands to control stimulus application hardware for controlling activity at such individual address.

Many of such aspects of the invention can be directly translated for use with parallel, serial or serial-parallel protocols. In a most preferred embodiment, for example, a rapid serial force system and protocols for that system can be used for characterization of materials with very high sample throughput.

Permeability

The systems and methods of the present invention include the ability to determine intrinsic properties exhibited by members of a library of materials with a particular ability to analyze permeability of a sample, such as fluid permeability of a polymer film such as permeability. According to one embodiment of the invention, a sample (or library of samples) is preferably exposed to one or more fluids. Responses of the material samples to such fluids are monitored. Permeability of any material samples is correlated with the responses of the material samples. Optionally, the material samples may be ranked relative to each other based upon their responses.

Figure 7:
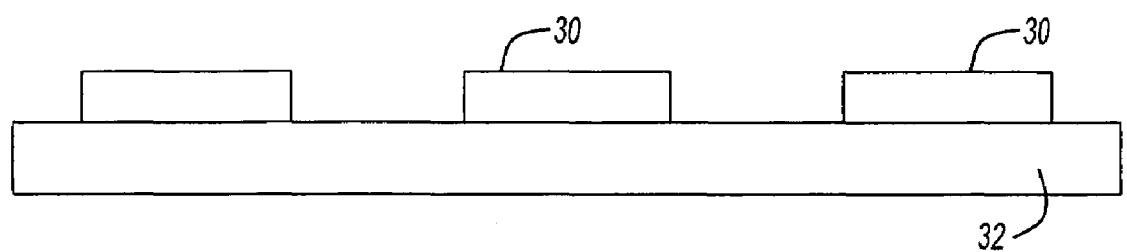
FIG. 7 illustrates samples supported on a permeable material according to an aspect of the present invention.

Preferably, the material samples are films and more preferably the materials are polymeric films. As used herein, the term "film" is intended to encompass a relatively thin layer, such as less than about 1 mm, and more preferably less than about 0.1 mm of material. Preferably, a film includes opposing surfaces and one or more thicknesses therebetween such that a fluid may permeate through the film from one surface to the other. According to one embodiment, the material samples may include coatings such as oil coatings, paint coatings, plasma coatings or the like. Moreover, as shown in FIG. 7, it is contemplated that the films 30 include or be disposed adjacent or proximate to a highly permeable material 32. Such a highly permeable material may act as merely a support of the samples for assisting in screening a coating disposed on the highly permeable material. Though preferably employed for analyzing films, the invention is not limited to films, but may be suitable for analyzing other masses of materials.

The material samples may be supplied separately or together and the samples may be supported by a plurality of substrates or a singular common substrate. The samples may be secured to a substrate with one or more adhesives, one or more fasteners, one or more portions of the substrate or the like. According to a preferred embodiment, a plurality of samples are provided on a common substrate by clamping the portions of the samples between a first member and a second member wherein the first member is movable relative to the second member. In such an embodiment, it is contemplated that the first and second member of the substrate may be separable or integral with each other.

Typically, the samples are secured to a substrate such that one or more surface of the samples are exposed (i.e., not contacting any solid members particularly of the substrate). Preferably, the samples are secured to one or more substrates within, adjacent to, or partially covering one or more openings (e.g., cavities, chambers, through-holes or the like) defined by the substrate. In one preferred embodiment, the samples are secured to a substrate with a surface of each of the samples exposed to an opening of the substrate (i.e., an exposure opening) such that the surface of the sample may be exposed to a permeate fluid in the opening. Additionally or alternatively, a surface of each of the samples is exposed to an opening of the substrate (i.e., a sensor opening) wherein permeate fluid that permeates through the sample may enter such opening. It should be understood that each exposure openings and sensor openings may be a portion of a singular larger opening or may be separate openings.

The permeate fluids to which the material samples are exposed are preferably provided as gasses, liquids or a mixtures thereof, but may include solids. Preferably, the fluids include at least one material that can at least partially permeate through the material samples. According to one embodiment, the fluids are gasses such as air, nitrogen gas, hydrogen gas, or another gas (e.g. a relatively small molecular gas) or the like. The gasses may be pure or they may include one or more vapors (e.g., water vapor). According to another embodiment, the fluids may be liquids that include water, oil, vinegar, sugars, fruit juice, acid (e.g. citric acid, phosphoric acid, acetic acid, malic acid), a salt or the like. It is further contemplated that the permeate fluids may includes oxygen, nitrogen, argon combinations thereof or the like. Other exemplary permeate fluids may include hydrocarbons such as hexane, heptane, alcohols, ketones (e.g. acetone), gasoline or other petroleum by-products, kerosene, alkanes (such as methane, propane, butane or the like), combinations thereof or the like.

Various parameters of the fluid such as composition, concentration, temperature, pressure or the like may be changed with respect to time during testing or from sample to sample across a library of samples. Alternatively, all or substantially all of the parameters of the permeate fluid may be maintained substantially constant with respect to time during testing. The permeate fluid may be substantially heterogeneous, but is preferably substantially homogeneous.

If a plurality of permeate fluids are provided, the permeate fluids may be different from each other, but are preferably substantially the same or substantially identical. For different permeate fluids, several parameters such as composition, concentration, temperature, pressure or the like of the samples may be varied (e.g., increased or decreased) simultaneously or in series and may be varied with respect to time or otherwise.

Exposure of the material samples to the fluids preferably includes exposing a first surface of each of the material samples to a fluid such that the at least a portion of the fluid is provided an opportunity to permeate through at least a portion of each of the samples. Preferably, the permeate fluids are allowed to permeate from one surface of each of the samples through a thickness of the samples to a second preferably opposing surface of each of the material samples. In one embodiment of the invention, it is preferable for the second surfaces of each of the samples to remain substantially physically isolated from the permeate fluid until portions of the fluid that permeate through the samples contact the second surfaces of the samples. According to other embodiments, however, such second surfaces may be exposed to permeate fluid by other sources, under controlled circumstances. Of course, it is contemplated within the scope of the invention that one or more of the samples may be substantially or entirely resistant to permeation by the selected permeate fluid and may exhibit very limited or no permeation during testing or screening.

For exposing the material samples to permeate fluids, a variety of techniques or protocols may be employed. For example, permeate fluids, and particularly permeate liquid fluids may be dispensed to material samples by spraying, dripping, squirting, dabbing, brushing or the like the fluid upon a surface of the material sample. According to a preferred embodiment, one or more liquid permeate fluids are dispensed to one or more openings (e.g., an exposure opening) defined by a substrate such that the one or more permeate fluids contact a surface of each of the samples. As another example, permeate fluids, and particularly gaseous permeate fluids may be dispensed to material samples by spraying, flowing, pressurizing or the like the permeate fluid upon a surface of the material samples. According to another preferred embodiment, one or more gaseous liquid permeate fluids are dispensed to one or more openings (e.g., exposure openings), which are defined by a substrate and, which act as or co-act with as a gas-tight chamber for maintaining the gaseous permeate fluids in contact with a surface of the one or more samples.

It is further contemplated that temperatures of the permeate fluids may be elevated or lowered before and during exposure of the samples to the fluids. For example, the temperature of a permeate fluid may be elevated about the boiling point of that fluid or the temperature of a permeate fluid may be lowered below the freezing point of the fluid. Moreover, temperatures of the samples may be lowered or elevated.

The response of the material samples to exposure to the permeate fluids is typically at least related to the permeation of at least a portion of the permeate fluids into and/or through the material samples. Preferably, the response of the material samples is a degree of permeation allowed by the material samples wherein the degree of permeation of the material samples gives an indication of (e.g., can be correlated to) the permeability of the samples to the permeate fluids. As examples, the degree of permeation may be exhibited as the rate at which a permeate fluid permeates into a material sample, through a material sample, or both. Alternatively, the degree of permeation may be exhibited by the distance to which a permeate fluid permeate into a material sample. As still another alternative, the degree of permeation may be exhibited by the amount of permeate fluid that permeate to and/or through the material sample.

One or more sensors (e.g., transducers) are typically employed for monitoring of the responses of the material samples to exposure to the permeate fluids. The sensors may monitor the samples directly. For example, material samples may be exposed to one or more permeate fluids for an amount of time (e.g., a predetermined period of time) followed by directly analyzing the samples to determine how much permeate fluid actually permeated into and/or through the samples. Alternatively, the sensors may monitor the samples indirectly. For example, the sensors may monitor a fluid or member that will exhibit varying characteristics depending upon the degree of permeation experienced by the material sample. Combinations of these approaches may also be used.

It is contemplated that a large variety of sensors may be employed for the systems and methods of the present invention. The sensors may be configured for the detection of one or more particular materials (e.g., the permeate fluid or a material thereof), such sensors are referred to herein as material-specific sensors. Examples of material specific sensors include, without limitation, humidity sensors for detecting moisture content within a fluid, oxygen detectors, carbon monoxide detectors, ion-specific detectors, other electronic or chemical sensors or the like. The sensors may also be configured for the detection of one or more non-specific materials, such sensors are referred to herein as non-material specific sensors. Examples of non-material specific sensors include, without limitation, pressure sensors, spectroscopic detectors, materials such as activated carbon, pH sensors or the like. Other chemical sensors include adsorbent or absorbent materials that adsorb or absorb permeate fluids or other materials over time or depending upon concentrations of the permeate fluids or other materials.

Alternative sensors may detect electric properties such as impedance, resistant, dielectric constant or the like. Other possible sensors may employ magnetic detection, ultrasonic detection, infrared (IR) thermography (e.g., fourier transform IR thermography). Still, other possible sensors such hygroscopicity microbalance, tuning forks or the like may be employed in the present invention, particularly where the samples have a functionalized surface. Examples of such sensors or methods of sensing are disclosed in commonly owned patent applications Ser. No. 10/155,207, May 24, 2002, titled "High Throughput Microbalance and Methods of Using Same"; Ser. No. 08/946,135, filed Oct. 7, 1997 "Infrared Sprectroscopic Imaging of Libraries; U.S. Pat. No. 6,393,895; both of which are incorporated by reference for all purposes. Still other examples of sensors or methods of sensing are disclosed in U.S. Pat. No. 6,393,895, titled "Method and Apparatus for Characterizing Materials by Using a Mechanical Resonator" also incorporated herein by reference for all purposes.

Such sensors may be configured for measuring amounts of permeation over time, amount of time to reach a certain predetermined level of permeation, changes in rate of permeation over time, combinations thereof or the like. Furthermore, the sensor may be openly exposed or partially or fully housed (e.g., behind a protective shield, baffle, screen or the like).

In one embodiment, the sensors of the present invention may include a permeation responsive material that changes visually depending upon the permeation experienced by the samples. For example, a sensor may comprise a permeation responsive material such as an adsorbent or absorbent material that changes color or other features at least partially in response to adsorption or absorption of permeate fluid such that the change can be related to an amount or rate of permeate fluid passing through a material sample. The sensor may also comprise an optical detector such as a fiber optic cable connected to an optical spectrometer for monitoring the changes in the adsorbent or absorbent material.

In an alternative embodiment, a sensor may comprise a permeation responsive material such as an adsorbent or absorbent material that may be analyzed after a period of time of absorption or adsorption. In such an embodiment, the permeation responsive material (e.g., the adsorbent material) is allowed to respond (e.g., adsorb) permeate fluid that has permeated through a material sample over a period of time. Thereafter, the permeation responsive material is analyzed via a variety of techniques to gain data or information regarding the degree for permeation allowed by the sample. Techniques for analyzing such materials include, without limitation, color measurement, high pressure liquid chromatography HPLC, size exclusion chromatography SEC, refractive index determination. Alternatively, the permeation responsive materials may be analyzed by chemical development (e.g., chemical conversion) of the permeation responsive materials into a condition suitable for detecting. For example, a permeation responsive material might be chemically developed into a colored material, the spectral characteristics of which can be related to the amount of permeated material deposited on permeation responsive material. As another alternative, the permeate material deposited on a permeation responsive material may be liberated from the permeation responsive material into another medium followed by detections of the permeate material in the new medium. For example, the permeation responsive material may be an adsorbent material, which releases permeation fluid as a gas when heated such that the gas can be quantitatively analyzed in a mass spectrometer.

Determination of the permeabilities of the material samples may be direct from the responses of the material samples (i.e., the responses themselves may be an adequate quantification of the permeability of the samples). Alternatively, the responses may be manipulated according to mathematical or empirical equations for correlating the responses to the permeability of the samples. As used herein, determination or correlation of permeabilities is meant to include relative permeabilities of the samples with respect to each other, relative indications of the permeabilities of the samples with respect to each other, and actual quantifications of permeabilities of the samples.

Figure 3:
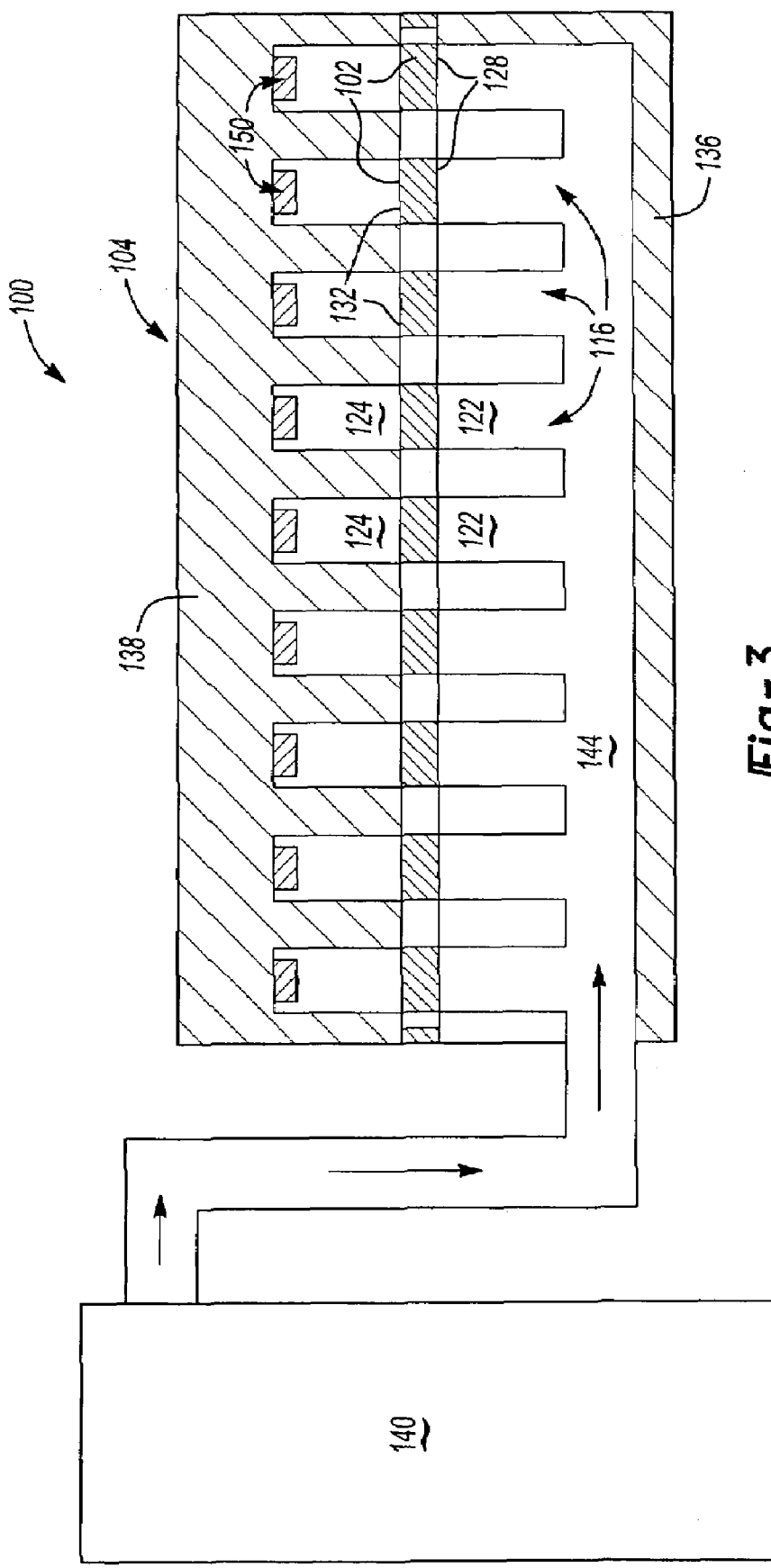
FIG. 3 is a schematic of a system for assisting in determining permeability of materials in accordance with the present invention.

Referring to FIG. 3 there is illustrated a schematic diagram of one exemplary system 100 for testing the permeability of a plurality of material samples 102. The system 100 preferably includes a substrate 104 for supporting the plurality of material samples 102. As shown, the material samples 102 are films, and particularly polymeric films, although it is contemplated that the samples 102 may be provided in variety of other configurations.

In a preferred embodiment, the substrate 104 includes a plurality of openings 116 such that each of the samples 102 may be at least partially located within its own opening 116.

In FIG. 3, each sample 102 is clamped within its own opening 116 such that the sample 102 divides its respective opening 116 into a first opening and a second opening herein referred to as an exposure opening 122 and a sensor opening 124. As shown, a first surface 128 of each of the samples 102 is exposed to the exposure opening 122 and a second surface 132 of each of the samples 102 is exposed to the sensor opening 124 of the openings 116. The samples 102 may be secured within the openings 116 in a variety of ways. In the embodiment shown, the films 102 are clamped between a pair of members 136, 138 wherein one member 136 defines the exposure openings 122 and another member 138 defines the sensor openings 124. The members 136, 138 may be formed of a variety of materials, but are preferably formed of a plastic or a metal such as aluminum.

Preferably, the substrate 104 is in fluid communication with one or more fluid sources 140 for exposing the samples 102 to one or more fluids. As depicted, the substrate 104, particularly the first member 136, defines a manifold 144 (i.e., an open space substantially enclosed by the substrate) in fluid communication with the fluid source 140 for receiving fluid therefrom. Preferably, the manifold 144 is below the samples 102 although it may be positioned above the samples 102 or elsewhere. It is also preferable for the manifold 144 to be in fluid communication with each of the exposure openings 122.

The system 100 also preferably includes at least one, but preferably a plurality of sensors 150 associated with the samples 102, the sensor openings 124 or both. While it is preferable for the sensors 150 to be associated with sensor openings 124, it is contemplated that the sensors 150 may be in direct contact with the samples 102 and the sensor openings 124 may be eliminated or may only provide enough space to house the sensors 150. It is further contemplated that the sensor may be positioned in a variety of locations within the sensor openings 124 such as along a side wall defining the opening 124, in opposing relations to the sample 102, suspended with the opening 124 or the like. In the particular embodiment shown, the substrate 104 supports the sensors 150 with at least one sensor 150 positioned within each of sensor openings 124. For the system 100 of FIG. 3, the sensors 150 are adsorbent materials that can adsorb materials of permeate fluids, which permeate through the samples 102.

In operation, the fluid source 140 supplies fluid to the manifold 144, which supplies fluid to the exposure openings 122 for exposing the first surfaces 128 of the samples 102 to the fluid. Over time, the samples 102 respond by allowing at least a portion of the fluid to permeate from the first surface 128 through the samples 102 to the second surface 132 and into the sensor openings 124.

In turn, the sensors 150 provide information or data from which at least the relative permeabilities of each of the samples 102 may be determined or, more particularly, the amount (e.g., relative amount) of fluid that permeates through each of the samples 102 for a given amount of time may be determined. For the embodiment depicted, the sensors 150 (i.e., the adsorbent materials) adsorb amounts of the fluid in proportion to the concentration of the fluid in the sensor portions 124 wherein the concentration of the fluid in the sensor portions 124 is proportional or empirically correlated to the amount of fluid that permeates through the samples 102 (e.g., the permeability). Thus, the permeability of each of the samples 102 may be determined by analyzing the amount of permeate fluid adsorbed by the sensors 150. Alternatively, the samp Thereafter, the amount of permeate fluid adsorbed by the sensors 150 may be determined according to a variety of protocols. For example, and without limitation, techniques such as material chemical development, through thermal emission and mass sensitive detection or the like may be used to determine the amount of permeate fluid adsorbed by the sensors 150. The absolute or relative permeabilities of the samples 102 may then be determined using standard engineering equations for permeability, adsorption, concentration or the like.

Figure 4B:
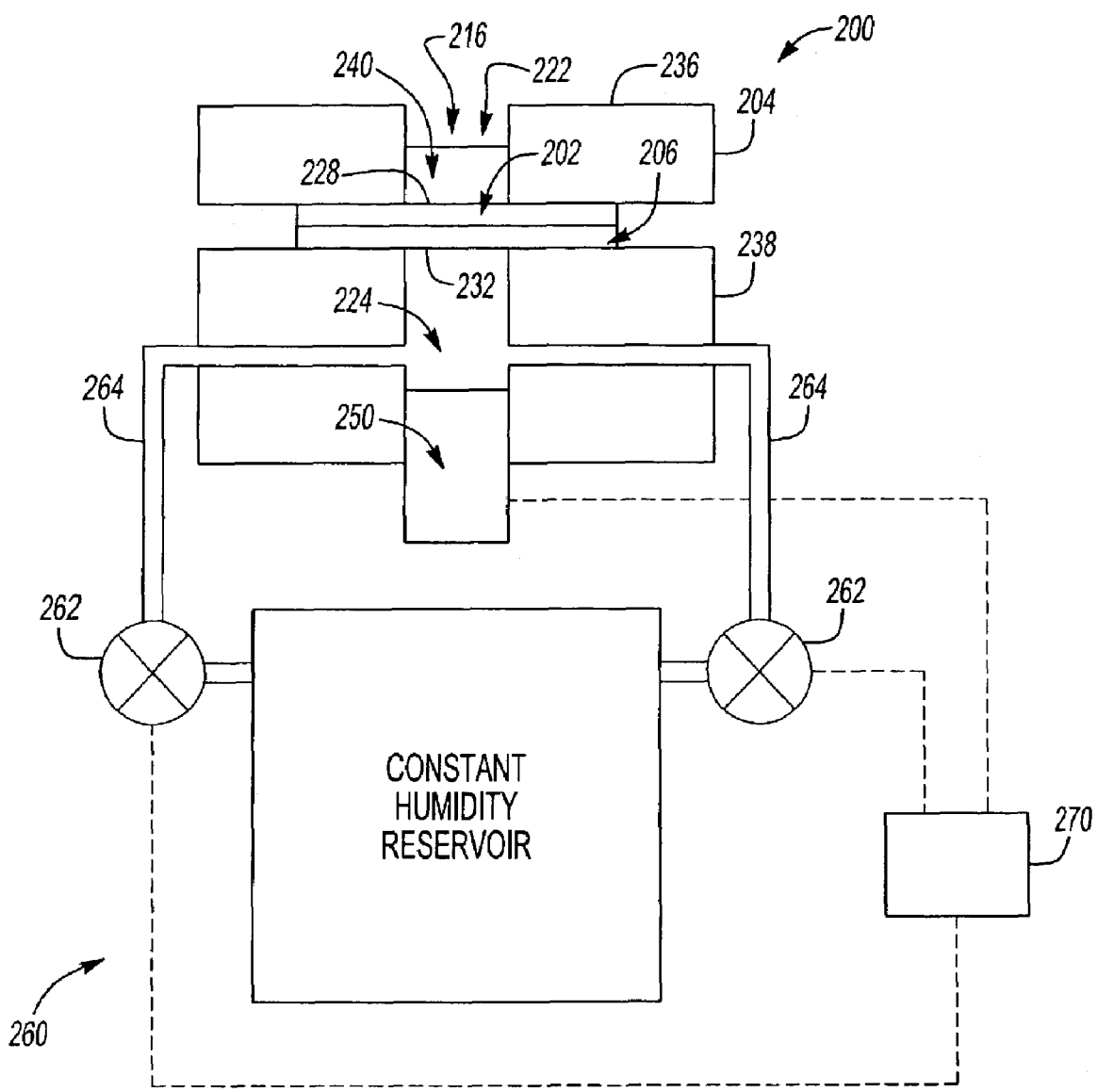

Referring to FIGS. 4A and 4B there is illustrated a schematic diagram of another exemplary system 200 for testing the permeability of a plurality of material samples 202. The system 200 preferably includes a substrate 204 for supporting the plurality of material samples 202. As shown, the material samples 202 are films, and particularly polymeric films, although it is contemplated that the samples 202 may be provided in variety of other configurations and as a variety of other materials. Also in the particular embodiment shown, the samples 202 include a coating 206 (e.g., a coconut oil layer) over at least a portion of surface of the polymeric film.

In a preferred embodiment, the substrate 204 includes a plurality of openings 216 such that each of the samples 202 may be at least partially located within its own opening 216. In FIGS. 4A–4B, each sample 202 is clamped within its own opening 216 such that the sample 202 divides its respective opening 216 into a first opening and a second opening herein referred to as an exposure opening 222 and a sensor opening 224. As shown, a first surface 228 of each of the samples 202 (e.g., of the polymeric film) is exposed to the exposure opening 222 and a second surface 232 of each of the samples 202 (e.g., of the coating) is exposed to the sensor opening 224. The samples 202 may be secured within the openings 216 in a variety of ways. In the embodiment shown, the films 202 are clamped between a pair of members 236, 238 of the substrate 204 wherein one member 236 defines the exposure openings 222 and another member 238 defines the sensor openings 224.

One or more permeate fluids 240 are contacted with the samples 202 such that at least a portion of the permeate fluids 240 can permeate through the samples 202. In the embodiment shown, the permeate fluids 240 are liquids (e.g., water) that are dispensed in the exposure openings 222 such that the first surface 228 of the samples 202 at least partially support the liquids. Preferably, the exposure openings 222 are above the samples 202 to assist in contacting the fluids with the first surfaces 228 of the samples 202 although they may be positioned below the samples 202 or elsewhere.

The system 200 also preferably includes at least one, but preferably a plurality of sensors 250 associated with the samples 202, the sensor openings 224 or both. While it is preferable for the sensors 250 to be associated with sensor openings 224, it is contemplated that the sensors 250 may be in direct contact with the samples 202 and the sensor openings 224 may be eliminated or may only provide enough space to house the sensors 250. In the particular embodiment shown, the substrate 204 supports the sensors 250 with at least one sensor 250 positioned within or exposed to each of sensor openings 224. For the system 200 of FIGS. 4A–4B, the sensors 250 are permeate fluid sensors (e.g., humidity sensors) that can sense the amount or percentage of permeate fluids 240, particularly water vapor, in the sensor openings 224, which, in turn, can assist in determining the amounts of permeate fluids 240 that permeate through the samples 202 over time. One exemplary humidity sensor is sold under the designation Honeywell IH-3602C and is commercially available form the Honeywell Corporation.

The system 200 of FIGS. 4A–4B also includes a purge sub-system 260 having valves 262 (e.g., solenoid valves, which may be switched on and off by mechanical relays or otherwise) and connectors 264 (e.g., piping) for flowing a purge fluid (e.g., dry nitrogen) from a purge fluid reservoir 268 into the sensor openings 224. Preferably, the valves 262 and sensors 250 are in signaling communication with a controller 270 (e.g., a computer system, a data acquisition board of a transistor or the like) for controlling the flow of the purge fluid to the sensor openings 224. In the preferred embodiment, the purge fluid has a substantially constant concentration of permeate fluid 240, which may be a total absence of permeate fluid or any other concentration.

In operation, the one or more permeate fluids 240 are dispensed in the exposure openings 222 for exposing the first surface 228 of each of the samples 202 to the permeate fluids 240. Over time, the samples 202 respond by allowing at least a portion of the permeate fluids 240 to permeate from the first surface 228 through the samples 202 to the second surface 232 and into the sensor openings 224. In turn, the amount or concentration of permeate fluid 240 in the sensor openings 224 increase and such increase is preferably sensed by the sensors 250.

In turn, the sensors 250 provide information or data from which, at least the relative permeabilities of each of the samples 202 may be determined or, more particularly, the amount (e.g., relative amount) of fluid that permeates through each of the samples 202 over time may be determined.

In a highly preferred embodiment, the valves 262 and sensors 250 of the purge sub-system 260 are in communication with the controller 270 during measurements of permeability for assimilating a substantially constant concentration of permeate fluid 240 in the sensor openings 224. For the embodiment, a pre-determined upper limit is set for the concentration of permeate fluid 240 in the sensor opening 224. Once enough permeate fluid 240 permeates through the sample 202 and raises the concentration of permeate fluid in the sensor opening 224 to the upper limit, the sensor 250 signals the controller 270, which signals the valves 262 to open. In turn, the purge fluid flows into the sensor opening 224 thereby replacing the permeate rich fluid in the sensor opening 224 with the purge fluid.

By setting the upper limit for the concentration of permeate fluid 240 in the sensor openings 224 relatively low (e.g., of a permeate fluid concentration no more than 10% greater than the purge fluid), a substantially constant concentration of permeate fluid 240 is assimilated in the sensor openings 224. For measuring purposes, the rate at which the sensor openings 224 must be purged to assimilate the constant concentration in the sensor openings 224 is monitored. In turn, the absolute or relative permeabilities of the samples 202 may then be determined by relating the rate of purging the sensor openings 224 to those permeabilities using standard engineering equation for permeability, concentration or the like.

As an alternative to setting an upper limit for purging the sensor openings, a microcontroller, which opens and closes the valves based upon a control algorithm may be employed. Preferably, the output of the microcontroller, which may be expressed in units of "duty cycle", is proportional to the rate at which the permeate fluid diffuses through the sample.

Advantageously, assimilating a substantially constant concentration of permeability in the sensor opening assures that permeation through the samples is driven by the concentration of permeation fluid in the exposure openings rather than being effected by the concentration of permeation fluid in the sensor opening. Moreover, the sensors don't become saturated such that comparative measurements between the permeability of the samples may be more effectively measured since saturation of the sensors does not effect the quantification of permeation fluid passing through the samples.

Figure 5:
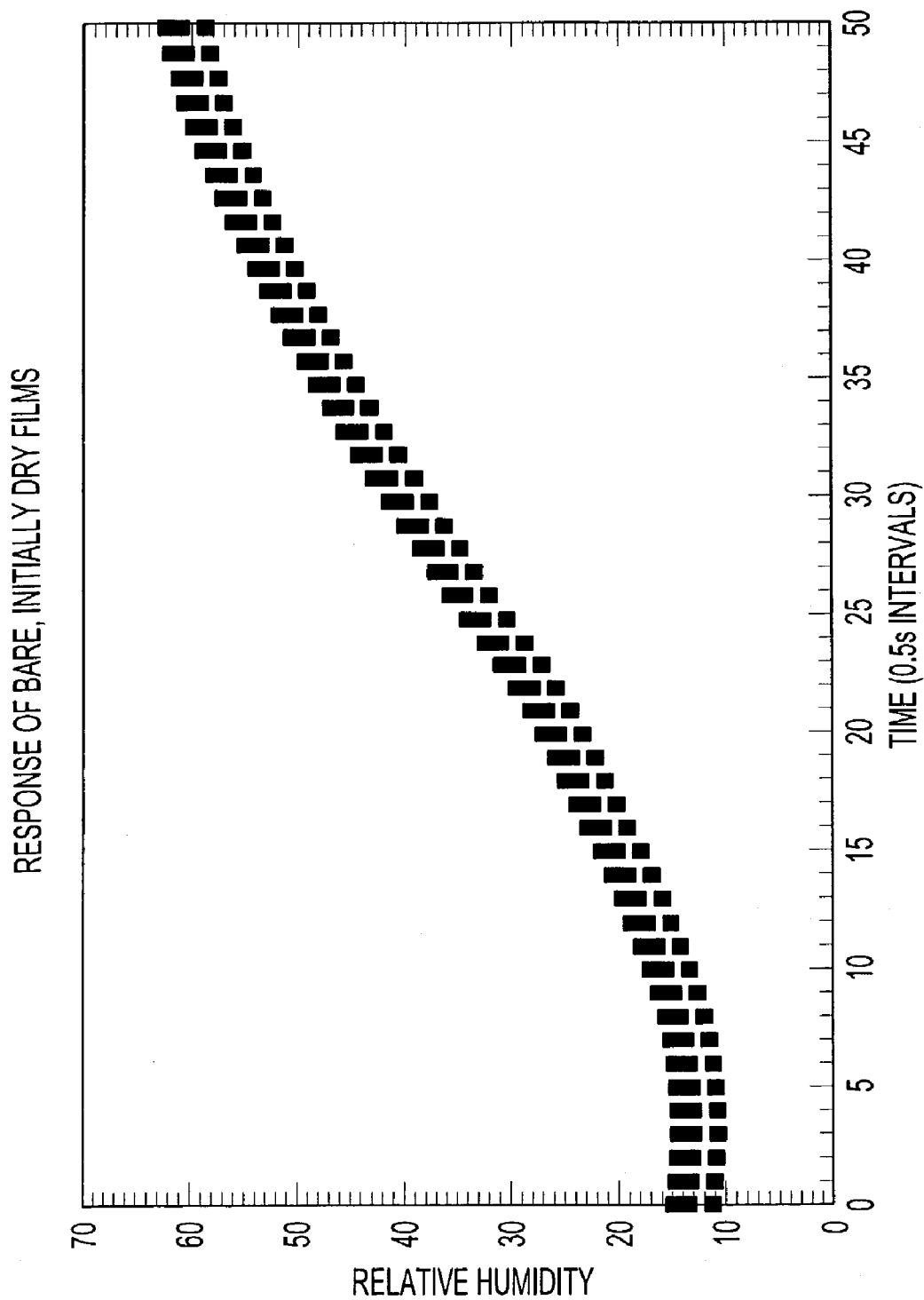
FIG. 5 is a graphical representation of data resulting from samples tested according to aspects of the present invention.
Figure 6:
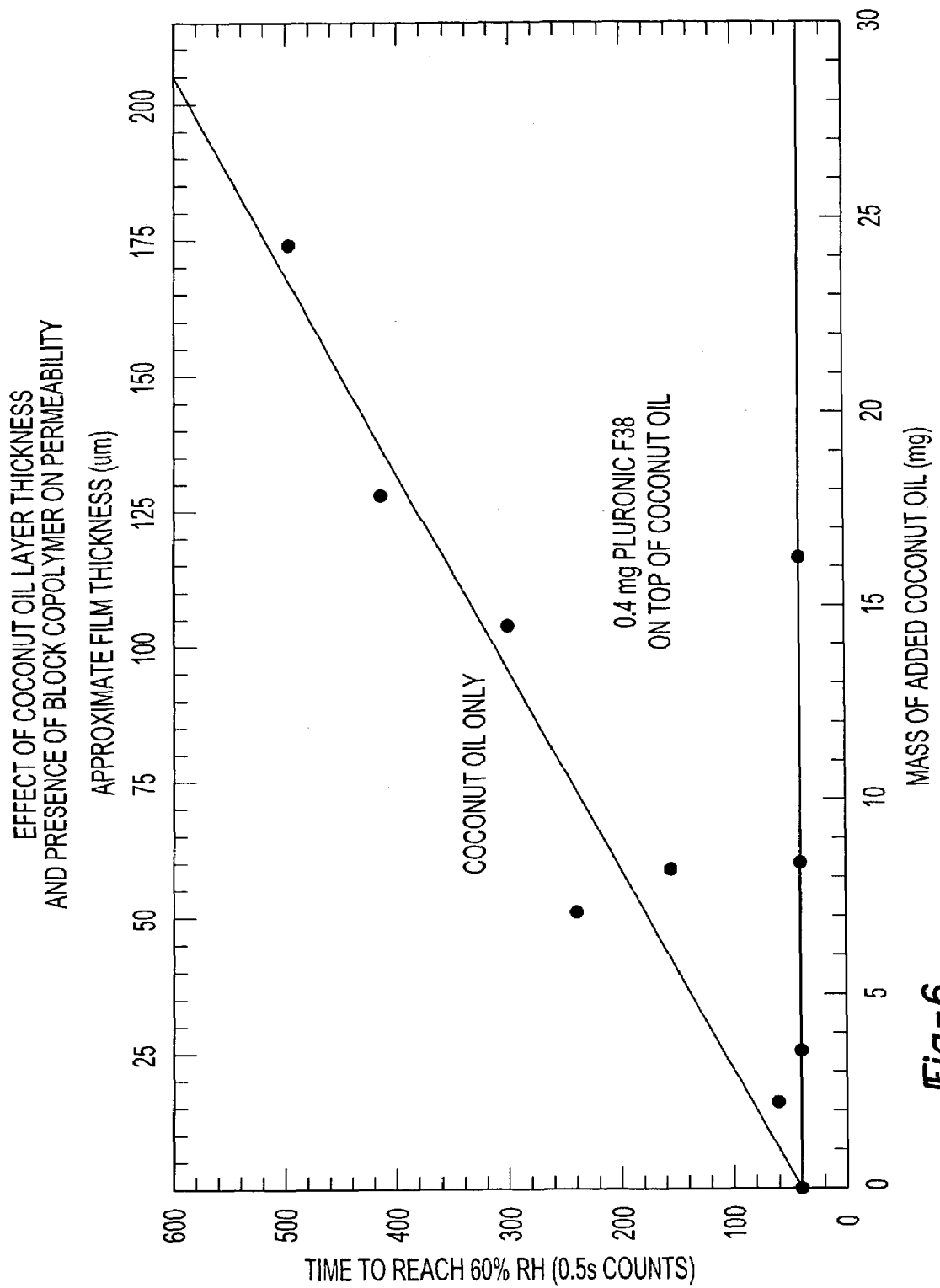
FIG. 6 is also a graphical representation of data resulting from samples tested according to aspects of the present invention.

As examples, FIGS. 5 and 6 illustrate graphs of data, which might be provided by a system according to the present invention. For FIG. 5, samples (e.g., dry polymeric films) are exposed to high humidity air contained within exposure openings. Over time, water (e.g. deionized water) vapor permeates through the samples to sensor openings thereby raising the relative humidity in the sensor openings. Thus, FIG. 5 shows a graph of humidity in the sensor openings over time.

For FIG. 6, samples are also exposed to high humidity air contained within exposure openings. The particular samples are polymeric films coated with variable amounts of coconut oil. Preferably, measures are taken to level the coconut oil the polymeric films such as heating the oil. Over time, water vapor permeates through the samples to sensor openings. Thus, FIG. 6 shows a graph of humidity is the sensor openings with respect to time, film thickness and amount of coconut oil on the films.

In addition to combinatorial chemistry, it is also contemplated that the instruments of the present invention may be employed in other applications as well. For example, the instruments may be adapted for performing on-line permeability measurements at a manufacturing facility for maintaining quality control over industrial films such as cellophanes, films for plastic bags or the like. As an alternative example, the instruments may be employed for measuring permeability of samples over large periods of time to assure that certain materials resist deterioration over such time periods.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

Calibration Methods and Standards

As desired the systems and methods of the present invention may optionally employ a calibration procedure. By way of example, a calibration standard is provided having a number of subcomponents that differ with respect to permeability of a material. Such subcomponents are typically referred to as "known standards" or, simply, "standards" that are well characterized with respect to the calibrating property of interest. They are analyzed by the measuring apparatus of the present invention and the apparatus is adjusted as desired.

The accuracy and precision of the determination of material properties can vary depending on the type of measurement being conducted, the purpose of the measurements and the like. According to one embodiment the response, the stimulus or both applied to each of the material samples of the samples may be ranked or indexed and the ranked or indexed properties may be compared with each other. In such a case, accuracy and precision with regard to determining exact values of the properties of the sample materials may not be as important as assuring that the tests are performed consistently upon samples that are compared to each other since the object of the testing may be to determine which materials perform best rather than determining exact material properties. In other cases, such as when the stimuli and responses of the sample materials will be used to compare the sample materials to known properties of known materials, it may be more important to determine values for sample material properties such as permeability and the like that are closer to the absolute values of those properties for the sample materials to allow useful comparisons. The skilled artisan will recognize that the methods and apparatuses discussed above can be configured to more or less accurate depending upon the equipment used and that the choice of equipment can depend on constraints such as monetary constraint and upon the amount of accuracy needed for a particular purpose.

Other Screens

The present invention may be employed by itself or in combination with other screening protocols for the analysis of liquids or their consitituents. Without limitation, examples of such screening techniques include those addressed in commonly-owned U.S. Pat. No. 6,406,632 (Safir et al.); U.S. Pat. No. 6,371,640 (Hajduk et al.); U.S. Pat. No. 6,182,499 (McFarland et al); U.S. Pat. No. 6,175, 409 B1 (Nielsen et al); U.S. Pat. No. 6,157,449 (Hajduk et al); U.S. Pat. No. 6,151,123 (Nielsen); U.S. Pat. No. 6,034, 775 (McFarland et al); U.S. Pat. No. 5,959,297 (Weinberg et al), U.S. Pat. No. 5,776,359 (Schultz et al.), all of which are hereby expressly incorporated by reference herein.

Screening techniques may also include (without limitation) optical screening, infrared screening, electrochemical screening, flow characterization (e.g., gas, liquid or gel-phase chromatography), spectrometry, crystallography, or the like.

It should be understood that the invention is not limited to the exact embodiment or construction which has been illustrated and described but that various changes may be made without departing from the spirit and the scope of the invention.

What is claimed is:

1. A method for screening an array of materials for permeability, the method comprising:
   providing a library of at least four material samples, each of the at least four samples including a first surface and a second surface;
   exposing the first surface of each of the at least four material samples to at least one of a plurality of exposure openings;
   exposing the second surface of each of the at least four material samples to at least one of a plurality of sensor openings, each of the plurality of sensor openings having at least one of a plurality of sensors associated therewith;
   introducing at least one permeate fluid into the plurality of exposure openings;
   monitoring any amount of the permeate fluid that accumulates in the plurality of sensor openings with the plurality of sensors;
   purging the permeate fluid from the plurality of sensor openings when the concentration of the permeate fluid rises to a predetermined level; and
   correlating a rate of purging the permeate fluid from the plurality of sensor openings to a permeability for each of the at least four material samples.

2. A method as in claim 1 wherein the at least four material samples are provided as polymeric films.

3. A method as in claim 2 wherein the step of providing the at least four samples includes supporting the at least four samples with a substrate.

4. A method as in claim 3 wherein the substrate includes the plurality of sensor openings and the at least four samples are disposed over the plurality of sensor openings.

5. A method as in claim 1 wherein the at least four samples are positioned upon a substrate by an automated system that includes a robot arm.

6. A method as in claim 1 wherein at least one permeate fluid includes water vapor and the plurality of sensors are humidity sensors for sensing the water vapor.

7. A method as in claim 1 further comprising raising the temperature of the at least four material samples such that the at least four samples are at an elevated temperature during exposure to the permeate fluid.

8. A method as in claim 1 further comprising lowering the temperature of the at least four material samples.

9. A method for screening an array of materials for permeability, the method comprising:
   providing a library of at least four material samples, each of the at least four samples including a first surface and a second surface, wherein:
   i. the at least four samples are positioned upon a substrate over multiple sensor openings of the substrate, each sensor opening associated with at least one sensor selected from an oxygen detector and a humidity sensor;
   exposing the first surface of each of the at least four material samples to at least one permeate fluid, the at least one permeate fluid including at least one of oxygen or water vapor;
   monitoring a response for each of the at least four material samples to the exposure to the at least one permeate fluid, the monitoring including;
   i. sensing, with the at least one sensor of each sensor opening, the amount of oxygen, water vapor or both of the permeate fluid that each of the at least four samples allows to pass into the sensor openings; and
   ii. purging, with a purge sub-system, the permeate fluid from the sensor openings when the amount of permeate fluid in the sensor openings reaches a predetermined level;
   determining a permeability for each of the at least four material samples based upon the response.

10. A method as in claim 9 wherein the at least four material samples are provided as polymeric films.

11. A method as in claim 9 wherein the at least four material samples are clamped to the substrate.

12. A method as in claim 9 further comprising raising the temperature of the at least four material samples such that the at least four samples are at an elevated temperature during exposure to the permeate fluid.

13. A method as in claim 9 further comprising lowering the temperature of the at least four material samples.

14. A method as in claim 9 wherein the at least four samples are positioned upon a substrate by an automated system that includes a robot arm.

15. A method as in claim 9 wherein each of the at least four material samples is a film having a thickness less than 0.1 mm and being supported upon the substrate by a highly permeable material.

16. A method as in claim 9 wherein determining the permeability for each of the at least four material samples includes monitoring rates at which the purge sub-system purges the sensor openings for assisting in determining absolute or relative permeabilities of the at least four samples.

17. A method as in claim 9 wherein:
   i. the at least four samples are positioned upon a substrate by an automated system that includes a robot arm;
   ii. each of the at least four material samples is a film having a thickness less than 0.1 mm and being supported upon the substrate by a highly permeable material;
   iii. determining the permeability for each of the at least four material samples includes monitoring rates at which the purge sub-system purges the sensor openings for assisting in determining absolute or relative permeabilities of the at least four samples.

18. A method for screening an array of materials for permeability, the method comprising:
   providing a library of at least four material samples, each of the at least four samples including a first surface and a second surface, wherein:
   i. the at least four samples are positioned upon a substrate over multiple sensor openings of the substrate, each sensor opening associated with at least one sensor selected from an oxygen detector and a humidity sensor; and
   ii. wherein the at least four samples are positioned upon a substrate by an automated system that includes a robot arm;
   exposing the first surface of each of the at least four material samples to at least one permeate fluid, the at least one permeate fluid including at least one of oxygen or water vapor;

monitoring a response for each of the at least four material samples to the exposure to the at least one permeate fluid, the monitoring including;
  i. sensing, with the at least one sensor of each sensor opening, the amount of oxygen, water vapor or both of the permeate fluid that each of the at least four samples allows to pass into the sensor openings; and determining a permeability for each of the at least four material samples based upon the response.

19. A method as in claim 18 wherein the at least four material samples are provided as polymeric films.

20. A method as in claim 19 wherein the at least four material samples are clamped to the substrate.

21. A method as in claim 19 further comprising raising the temperature of the at least four material samples such that the at least four samples are at an elevated temperature during exposure to the permeate fluid.

22. A method as in claim 19 further comprising lowering the temperature of the at least four material samples.

23. A method as in claim 19 wherein each of the at least four material samples is a film having a thickness less than 0.1 mm and being supported upon the substrate by a highly permeable material.

24. A method as in claim 19 wherein monitoring the response includes purging, with a purge sub-system, the permeate fluid from the sensor openings when the amount of permeate fluid in the sensor openings reaches a predetermined level.

25. A method as in claim 24 wherein determining the permeability for each of the at least four material samples includes monitoring rates at which the purge sub-system purges the sensor openings for assisting in determining absolute or relative permeabilities of the at least four samples.

26. A method as in claim 19 wherein:
  each of the at least four material samples is a film having a thickness less than 0.1 mm and being supported upon the substrate by a highly permeable material;
  ii. monitoring of the response includes purging, with a purge sub-system, the permeate fluid from the sensor openings when the amount of permeate fluid in the sensor openings reaches a predetermined level; and
  iii. determining the permeability for each of the at least four material samples includes monitoring rates at which the purge sub-system purges the sensor openings for assisting in determining absolute or relative permeabilities of the at least four samples.

* * * * *

UNITED STATES PATENT AND TRADEMARK OFFICE
CERTIFICATE OF CORRECTION

PATENT NO.       : 7,112,443 B2
APPLICATION NO.  : 10/274184
DATED            : September 26, 2006
INVENTOR(S)      : Hajduk et al.

It is certified that error appears in the above-identified patent and that said Letters Patent is hereby corrected as shown below:

Col. 23, Claim 21, Line 14, should be corrected to read, --A method as in claim 18 further...--

Col. 23, Claim 22, Line 18, should be corrected to read, --A method as in claim 18 further...--

Col. 23, Claim 23, Line 20, should be corrected to read, --A method as in claim 18 wherein...--

Col. 23, Claim 24, Line 24, should be corrected to read, --A method as in claim 18 wherein...--

Col. 24, Claim 26, Line 10, should be corrected to read, --A method as in claim 18 wherein:--

Signed and Sealed this

Ninth Day of January, 2007

JON W. DUDAS
*Director of the United States Patent and Trademark Office*